United States Patent [19]
Nagaraja et al.

[11] Patent Number: 5,455,034
[45] Date of Patent: Oct. 3, 1995

[54] FUSOBACTERIUM NECROPHORUM LEUKOTOXOID VACCINE

[75] Inventors: Tiruvoor G. Nagaraja; Muckatira M. Chengappa, both of Manhattan, Kans.

[73] Assignee: Kansas State University Research Foundation, Manhattan, Kans.

[21] Appl. No.: 78,066

[22] Filed: Jun. 18, 1993

Related U.S. Application Data

[63] Continuation-in-part of Ser. No. 905,041, Jun. 26, 1992, abandoned.

[51] Int. Cl.$^6$ .................. A61K 39/00; A61K 39/02
[52] U.S. Cl. .................. 424/236.1; 424/130.1; 424/164.1; 424/176.1; 424/184.1; 424/197.11; 435/71.3; 435/243; 435/252.1; 435/822
[58] Field of Search .................. 435/71.3, 243, 435/252.1, 822; 424/236.1, 176.1, 234.1, 130.1, 164.1, 184.1, 197.11

[56] References Cited

U.S. PATENT DOCUMENTS

| | | | |
|---|---|---|---|
| 4,152,415 | 5/1979 | Harris et al. | 424/262.1 |
| 4,203,968 | 5/1980 | Harris et al. | 424/203.1 |
| 4,919,929 | 4/1990 | Beck | 424/157.1 |

FOREIGN PATENT DOCUMENTS

0460480A2  11/1991  European Pat. Off. .

OTHER PUBLICATIONS

Emery, et al., 1986; Generation of Immunity Against *Fusobacterium Necrophorum* in Mice Inoculated with Extracts Containing Leucocidin, Vet. Microbiol. 12: 255–268.
Abe, et al., 1976; *Fusobacterium necrophorum* Infection in Mice as a Model for the Study of Liver Abscess Formation and Induction of Immunity, Infect. Immun. vol. 13, pp. 1473–1478.
Coyle–Dennis, et al., 1978; Biological and Biochemical Characteristics of *Fusobacterium necrophorum* Leukocidin; Am. J. Vet. Res., vol. 39, No. 11, pp. 1790–1793.
Warner, et al.;, 1974; Passive Hemmagglutination Test for Determining the Immunie Response of Rabbits to *Sphaerophorus necrophorus* of Bovine Hepatic Abscess Origin, Am. J. Vet. Res., vol. 35, No. 4, pp. 551–554.
Garcia, et al., 1975, Biological Characterization of *Fusobacterium necrophorum* Cell Fractions in Preparation for Toxin and Immunization Studies, 11:609–616, Infec. Immun.
Eemry et al., 1984, Biochemical and functional properties of a leucocidin produced by several strains of *Fusobacterium necrophorum*, Australian Vet. J., 61:382–385.
Scanlan et al., 1983, Bovine Rumenitis—Liver Abscess Comples: A Bacteriological Review, Cornell Vet. 73:288–297.
Emery et al., Studies on the Purification of the Leucocidin of *Fusobacterium Necrophorum* and its Neutralization by Specific Antisera, Vet. Microbiol, 11 (1986) 357–372.
Langworth, *Fusobacterium necrophorum*: Its Characteristics and Role as an Animal Pathogen, Bacteriol. Rev., 1977, 41:373–390.
Garcia, et al., Results of a Preliminary Trial with *Sphaerophorus necrophorus* Toxoids to Control Liver Abscesses in Feedlot Cattle, Can. J. com. Med, Jul., 1974, 38:222–226.
Abe et al Amer Jour Vet Res. vol. 39 No. 1 Jan. 1978 pp. 115–118.

*Primary Examiner*—Herbert J. Lilling
*Attorney, Agent, or Firm*—Hovey, Williams, Timmons & Collins

[57] ABSTRACT

A method is provided for the enhanced elaboration of leukotoxin from *F. necrophorum*, and subsequent production of an inactivated leukotoxoid ruminant animal vaccine against *F. necrophorum* infection and consequent liver abscesses and/or foot rot in such animals. The method involves forming a culture of *F. necrophorum* bacteria in growth media, allowing the bacteria to grow therein and to simultaneously elaborate leukotoxin in a supernate; the culturing is preferably carried out at a temperature of from about 35°–41° C., a pH of from about 6.5– 8, and for a period of from about 4–9 hours. At the end oil the culturing, bacterial growth and leukotoxin elaboration are terminated, preferably by separating the leukotoxin supernate, whereupon the vaccine is produced by inactivation of at least the supernate.

3 Claims, 3 Drawing Sheets

| 1A. | 1B. |

α — First Injection
β — Second Injection

- Tylosin
- Control
- Whole
- SPT+Ribi
- SPT+Stimuion
- Crude

FUSOBACTERIUM NECROPHORUM LEUKOTOXOID VACCINE

This application is a continuation-in-part application under 37 CFR 1.62 of prior application Ser. No. 07/905,041, filed on Jun. 26, 1992 now abandoned.

BACKGROUND OF THE INVENTION

1. Field of the Invention

The present invention is concerned with a method of enhancing the elaboration of leukotoxin from *F. necrophorum* (formerly *Sphaerophorus necrophorus*), in order to facilitate the preparation of an inactivated immunizing vaccine against liver abscesses and/or foot rot in ruminant animals, such as cattle and sheep. More particularly, it is concerned with such a method, as well as methods of producing the resultant vaccine and the vaccine itself, wherein a culture of *F. necrophorum* (preferably a biotype A strain) is grown with concomitant elaboration of leukotoxin as a supernate under specific conditions of temperature (preferably 35°–41° C.). pH (preferably 6.5–8) and time (preferably 4–10 hours) in order to maximize leukotoxicity. At the end of the culturing step, bacterial growth and leukotoxin elaboration are terminated and a vaccine is formed by inactivating at least the leukotoxin supernate.

2. Description of the Prior Art

Liver abscesses in feed lot cattle are a serious economic problem, causing condemnation of over 3 million livers and an estimated loss of $15 million annually in the United States. This estimate is based primarily on condemnation of liver and other organs, and does not include economic losses stemming from reduced feed efficiencies and lowered weight gains. A number of studies have confirmed that cattle with abscessed livers gain less (average 4–5%) and have reduced feed efficiencies (average 7%) compared with cattle having healthy livers. The average incidence of abscessed liver in grain-fed cattle approximates 25–30%.

*F. necrophorum* is the primary etiologic agent of liver abscesses in ruminant animals. The organism has been recognized as an animal and human pathogen since the late 1800s, and is associated with numerous necrotic disease conditions in domestic and wild animals. In addition to liver abscesses, the organism is also the primary etiologic agent of foot rot, foot abscesses, calf diphtheria, and is frequently isolated from cases of mastitis, metritis, and necrotic lesions of the oral cavity.

Liver abscesses in cattle are part of a disease complex where the abscessation is secondary to primary foci of infection in the rumen epithelium. The pathogenesis can be summarized as follows: (1) ruminal lesions are induced by acidosis that follows rapid change in diet from high-roughage to high grain, prolonged feeding of high grain diet, or occasionally by foreign body penetration of the rumen epithelium; (2) bacteria present in the rumen invade the epithelium and form focal abscesses in the rumen wall; and (3) bacteria enter the portal circulation, and are carried to the liver where they localize in the parenchyma with subsequent abscess formation.

The ability of *F. necrophorum* to establish in the liver is attributed to the production of a toxin called leukotoxin (or leucocidin). The toxin is soluble, proteinaceous and has specificity for bovine leukocytes. The leukotoxin is believed to aid in the establishment of *F. necrophorum* in the liver by directly impairing the normal defense mechanism and indirectly by the damage caused by cytolytic products released from neutrophils and macrophages to the hepatic cells. Therefore, the leukotoxin elaborated from *F. necrophorum* plays a critical role in *F. necrophorum* infection of the liver.

*F. necrophorum* is a gram-negative, nonspore-forming, nonmotile, strictly anaerobic and pleomorphic organism. Morphologically, the organism varies from short rods to filamentous with pointed and rounded ends. Cell lengths range from coracoid bodies of 0.5–0.7 µm in diameter to filaments over 100 µm. Surface colonies are 1–2 mm in diameter, circular, transparent to opaque, and with some strains producing α or β hemolysis. The organism ferinents glucose, fructose and maltose only weakly with final pH around 5.0–6.3. It ferments lactate to acetate, propionate, and butyrate. Butyrate is the major product from lactate fermentation. Indole is produced from peptlone. *F. necrophorum* has been isolated from the normal floca in the oral cavity, gastrointestinal cavity, and genitourinary tract of humans and animals. The organism is also known to survive in the soil.

Four biotypes (A, B, AB and C) of *F. necrophorum* have been described. Biotype A, most frequently isolated from liver abscesses, is more pathogenic than biotype B, which predominates in ruminal wall abscesses. Biotype AB is rarely isolated, and has pathogenicity intermediate that of biotypes A and B. Biotype C is non-pathogenic.

It has been suggested in the past to utilize *F. necrophorum* bacterin as an agent for immunizing cattle and sheep against liver necrosis, EPO Application No. 460480 of Dec. 11, 1991. Specifically, virulent *F. necrophorum* isolates are inactivated using B-propiolactone, followed by addition of adjuvants. In addition, Abe et al. (Infection and Immunity, 13:1473–1478, 1976) grew *F. necrophorum* for 48 hours. Cells were obtained by centrifuging, washing three times with saline, and were inactivated with formalin (0.4% in saline). The inactivated cells were then injected into mice to induce immunity. Two weeks after the last booster injection, each mouse was challenged with viable cells of *F. necrophorum*. The mice immunized with killed cells and challenged with live cells had no detectable bacteria in the liver, lung or spleen for up to 28 days. It was concluded that immunization of mice with formalin-killed *F. necrophorum* conferred protection against infection. Garcia et al. (*Canadian J. Comp. Med*, 38:222–226, 1974) conducted field trials to evaluate the efficacy of alum-precipitated toxoids of *F. necrophorum*. The vaccine preparation consisted of washed cells (unlikely to contain leukotoxin) that were ruptured by sonication. The most promising result was achieved with the injection of 15.5 mg protein of cytoplasmic toxoid. In this group, the incidents of liver abscesses was reduced to 10% from an average 35% in the control group. Finally, Emery et al., (*Vet. Microbiol.*, 12:255–268, 1986) prepared material by gel filtration of 18-hour culture supernate of *F. necrophorum*. This elicited significant immunity against challenged from viable *F. necrophorum*. The injected preparation contained endotoxin and the majority of the leukotoxic activity.

SUMMARY OF THE INVENTION

The present invention is predicated upon the discovery that prevention of leukotoxin production (or inhibition of its activity) in immunized animals will prevent the establishment of *F. necrophorum* infection. Thus, immunization of the animals against *F. necrophorum* leukotoxin, so that the animals' white blood cells or tissue macrophages may phagocytize the bacteria, presents an effective way to prevent diseases associated with *F. necrophorum* infection, e.g., liver abscesses in cattle and sheep, and foot rot in cattle.

In order to produce the most effective leukotoxoid vaccine, the *F. necrophorum* bacteria should be cultured in a way to enhance the elaboration of leukotoxin in the supernate. Thereupon, bacterial growth and leukotoxin elaboration may be terminated, and an effective vaccine prepared by inactivating at least the leukotoxin supernate.

In more detail, the leukotoxin elaboration method of the invention involves first forming a culture of *F. necrophorum* bacteria in growth media, and thereafter causing the bacteria to grow in the culture and to simultaneously elaborate leukotoxin in the supernate. The culturing should be carried out at a temperature of from about 35°–41° C., and most preferably about 39° C. In addition, the pH of the culture should be maintained at a level of from about 6.5–8, and most preferably about 6.7. The culturing period should be from about 4–10 hours, more preferably from about 4–9 hours, and most preferably from about 6–9 hours, in order to maximize production of leukotoxin. It is believed that continuing bacterial growth beyond about 10 hours results in the production of proteolytic enzyme(s) produced by the bacteria which degrade the toxin. *F. necrophorum* is known to produce proteolytic enzymes, and because the leukotoxin is proteinaceous, inactivation by such enzymes would account for the precipitous decline in leukotoxicity after about 10 hours.

Preferably, the selected *F. necrophorum* strain should be a biotype A strain thereof, inasmuch as such strains are known to be the most virulent. Particularly good results have been obtained with a specific *F. necrophorum* biotype A strain referred to herein as "strain 25." This strain has been deposited with the American Type Culture Collection, of 12301 Parklawn Drive, Rockville, Md. 20852, USA and has been accorded ATCC Accession No. 55329.

In particularly preferred forms of the invention, the culture medium should be selected from the group consisting of brain-heart infusion (BHI) and liver infusion broths. The media should also preferably include an iron concentration therein of from about 0.2–50 µM. These media are well known and are commercially available in the art. Moreover, the culturing should be carried out under anaerobic conditions, with an oxidation reduction potential of from about −230 to −280 mV. Anaerobic conditions are preferably achieved by boiling the medium, cooling under nitrogen gas, and reducing the medium by adding 0.05% cysteine hydrochloride. The medium is then dispensed anaerobically and autoclaved.

At the end of the culturing step, i.e., at the end of the selected culture time within the range of from about 4–10 hours, the bacterial growth and leukotoxin elaboration are terminated, and the leukotoxoid vaccine is prepared. Advantageously, this involves first separating the leukotoxin supernate from the bacteria, followed by inactivation through use of formalin, β-propiolactone, heat, radiation or any other known method of inactivation. Alternately, the entire culture may be inactivated to form the vaccine.

DETAILED DESCRIPTION OF THE PREFERRED EMBODIMENTS

The following examples describe the preferred techniques for the elaboration of *F. necrophorum* leukotoxin, as well as the subsequent production of leukotoxoid vaccine. It is to be understood, however, that these examples are presented by way of illustration only, and nothing therein should be taken as a limitation upon the overall scope of the invention.

EXAMPLE 1

The following example describes a series of tests undertaken to determine the conditions for maximal elaboration of leukotoxin from various strains of *F. necrophorum*. Full citations for referenced articles appear at the end of the description.

Bacterial Strains and Culture Techniques

Twenty-four *F. necrophorum* strains (9 biotype A and 15 biotype B) previously isolated from bovine liver abscesses (Lechtenberg et al., 1988) and strains 2159 and 5076 (biotype A) and 5111 (biotype B) obtained from Dr. John Berg, University of Missouri, Columbia, were used. Bacteria were grown in prereduced (0.05% cysteine HCl), anaerobically sterilized, BHI broth (DIFCO Laboratories, Detroit, Mich.) at 39° C. The anaerobic techniques used for preparation and dispensing of medium, inoculation, and sample removal were according to Holdeman et al. (1977). To minimize variation, the log-phase (determined spectrophotometrically) bacterial growth was used as inoculum in all experiments. Colony counts of *F. necrophorum* were determined in anaerobic BHI agar by the Hungate roll tube method (Hungate, 1969). Growth was monitored spectrophotometrically at A660 initially and at 1 hour intervals until maximum absorbance was recorded. Specific growth rate was calculated according to Koch (1981).

Leukotoxin Assay

Culture supernate for leukotoxin assay was obtained by centrifugation at 15,000×g for 30 minutes at 4° C. The supernate was filtered through a 0.2-µm membrane filter (Micron Separations, Inc., Westborough, Mass.) and mixed with an equal volume of phosphate-buffered saline (PBS; pH 7.4). Samples were stored at −70° C. and assayed for leukotoxicity. Leukotoxicity was quantitated by a tetrazolium (MTT)-dye (3-[4,5-dimethylthiazoyl-2yl]-2,5-diphenyltetrazolium bromide) reduction assay with bovine polymorphonuclear neutrophil (PMN) leukocytes as target cells (Vega et al., 1987). Blood PMN cells were isolated as described by Reddy et al. (1990). Briefly, blood was collected from the jugular vein into heparinized tubes and centrifuged at 1,500 x g for 10 minutes at 40° C. Plasma, buffy coat layer, and one-third of red blood cells (RBC) layer were discarded. The sediment containing PMN was treated with 0.83%-ammonium HCl (in 10 mM tris buffer, pH 7.5) for 1 minute to lyse remaining RBC, then was mixed with 20 ml of RPMI-1640 (GIBCO Laboratory, Grand Island, N.Y.). After centrifugation at 500 x g for 10 minutes, the pellet was collected and retreated with ammonium HCl. Isolated PMN were suspended in RPMI-1640 medium, supplemented with fetal bovine serum (5%), L-glutamine (1 mM), penicillin (5,000 U/ml) and streptomycin (5,000 µg/ml), at a final concentration of $2.5 \times 10^6$ PMN cells/mi. Cell concentration and viability (>97%) were determined by the trypan blue dye exclusion method.

One hundred µl of PMN suspension was dispensed into each well of a 96-well, flat-bottomed, cell culture microtitration plate and incubated overnight in 5% $CO_2$ humidified air atmosphere at 37° C. to allow adherence of neutrophils. After incubation, the medium was aspirated with a vacuum pump from each well to remove nonadherent cells and replenished with 100 µl of RPMI-1640 medium. An equal volume of serially diluted culture supernates was added into each well containing the neutrophils. The mixtures were incubated for 1 hour followed by addition of 20 µl of 0.5% (w/v) MTT-dye (Sigma Chemical Co., St. Louis, Mo.) per well. After 3 hours incubation in 5% of $CO_2$ at 37° C., the formazan concentration representing viability was determined by measuring absorbance in an ELISA reader with dual wavelength (570 nm as test wavelength and 650 nm as reference). The leukotoxicity, expressed in percentage of cell death, was calculated as follows:

(1 - absorbance of toxin-treated cells/absorbance of control cells)× 100

The titer of leukotoxin was calculated as the reciprocal of the culture supernate dilution causing 10% loss in viability of leukocytes.

Leukotoxin Production in Growth Stages and By Biotypes

To evaluate the time course of leukotoxin production, *F. necrophorum* biotype A strains 21 and 25 and biotype B strains 16 and 35 were grown in 100 ml of anaerobic BHI broth. Five ml aliquots were collected at 0, 2, 4, 6, 8, 10, 12, 16 and 29 hours for colony counts and toxin assay. Because leukotoxin production peaked at late-log phase (6–8 hours) of growth of both biotypes, subsequent samples for leukotoxin assay were obtained at late-log phase (6–8 hours), unless otherwise specified. To compare leukotoxin production between biotypes, 27 *F. necrophorum* strains (11 biotype A and 16 biotype B) were grown in anaerobic BHI broth. Culture supernates from late-log phase were assayed for leukotoxicity.

Effect of Culture Medium, pH and Incubation Temperature on Growth and Leukotoxin Production

*F. necrophorum* biotype A, strain 25 was grown under different cultural conditions. In order to select a suitable commercial medium that would support maximal leukotoxin production, bacteria were grown in BHI, Eugon, and Liver infusion broths (DIFCO) at 39° C. All growth media were prereduced with cysteine hydrochloride and sterilized anaerobically. The inocula were obtained by growing the bacteria in the same medium. To evaluate the effect of medium pH on growth and leukotoxin production, bacteria were grown in anaerobic BHI broth with pH of 6.7, 7.3, 7.7, and 8.2 at 39° C. Medium pH was adjusted by adding 1 N NaOH or 1 N HCl. To compare the growth and toxin production under various incubation temperatures, bacteria in anaerobic BHI broths (pH 7.7) were incubated 30, 35, 39 and 43° C. In all instances, samples for leukotoxin assay were obtained at 6–8 hours of incubation period (late log phase).

Effect of Eh on Growth and Toxin Production

The Eh of BHI broth was adjusted by adding an oxidizing agent, 0.20 M-potassium ferricyanide (Fisher Scientific), or reducing agents, 0.06 M-cysteine HCl, 0.13 M-dithiothreitol (DTT; Sigma Chemical Co., St. Louis, Mo.), or 0.10M-titanium (III) citrate (TC; Fisher Scientific, Fair Lawn, N.J.) through a programmable, microprocessor controlled pipette (Hamilton Bonadaz AG, Switzerland). Eh was measured with a platinum combination electrode with Ag/AgCl as reference (Corning Glass Works, Corning, N.Y.). The electrode was calibrated by adjusting the Eh value to 86±10 mV in a 0.05 M-potassium phosphate monobasic sodium hydroxide buffer (pH 7.0) saturated with quinhydrone (Eastman Kodak Co., Rochester, N.Y.) at 25° C. All measurements were performed in an anaerobic glove box (Forma Scientific, Inc., Marietta, Ohio). Eh values were calculated according to the following formula (Hentges and Maier, 1972; Segel, 1976):

$$EH_7 = E + 222 - 59 (pH_x - 7)$$

$EH_7$=the redox potential in relation to the hydrogen electrode at pH 7.0;

E=the redox potential value measured by platinum combination electrode with Ag/AgCl as reference;

$pH_x$=pH of the culture.

To determine the influence of Eh on growth and leukotoxicity, *F. necrophorum* strain 25 was grown in medium with Eh ranging from +375 to −352 mV. After 6–8 hours of incubation, samples were taken for leukotoxin assay.

Effect of Iron on Growth and Toxin Production

*F. necrophorum* strain 25 was grown in anaerobic BHI broth containing different concentrations of iron. All glassware and stoppers used in this experiment were soaked in 1 M HCl overnight and then rinsed thoroughly with deionized distilled water. Chelex 100 resin (50–100 mesh; Bio-Rad Laboratories, Rochville Center, N.Y.) was used to deplete iron from the medium by the method of Murphy et al. (1978) with the following exceptions; (i) a 5-g protein of resin was added to 100 ml of BHI broth and stirred for 1 hour; (ii) resin was removed by filtration, and the procedure was repeated twice, the resulting iron-limited medium (<0.2 µM) was supplemented with $Ca^{2+}$ and $MG^{2+}$ (6.0 mg of $CaCl_2.2H_2O$ and 2.2 mg of $MgSO_4$ per 100 ml of medium). Ferric chloride solution ($FeCl_3.6H_2O$) was added to the iron-limited medium to obtain concentrations of 4.2, 42.1 and 361.4 µM of $Fe^{3+}$. The medium was then boiled, added with cysteine HCl, and anaerobically sterilized. Iron content in the medium was determined in an atomic absorption spectrophotometer.

Statistical Analysis

Each experiment was replicated four times. Data was analyzed by the General Linear Models procedure of SAS (1987). Duncan's multiple range test was used for group comparison. The significance level for all analysis was $p<0.05$ unless otherwise stated.

RESULTS

Growth Phase

Figure 1A:
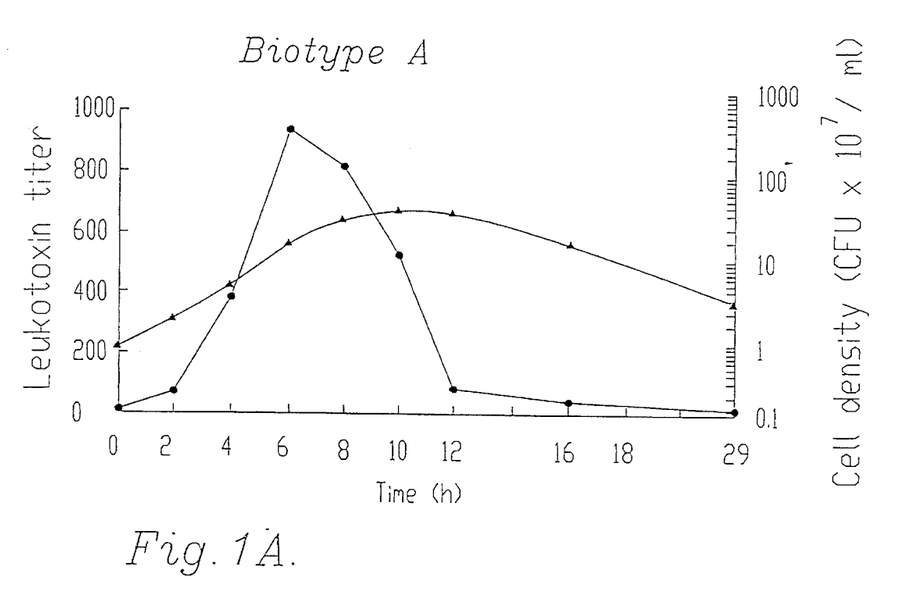
FIG. 1A is a graph illustrating leukotoxin production (dot data points) in relation to growth of a representative strain of biotype A of *F. necrophorum* (triangular data points), grown in anaerobic BHI broth.
Figure 1B:
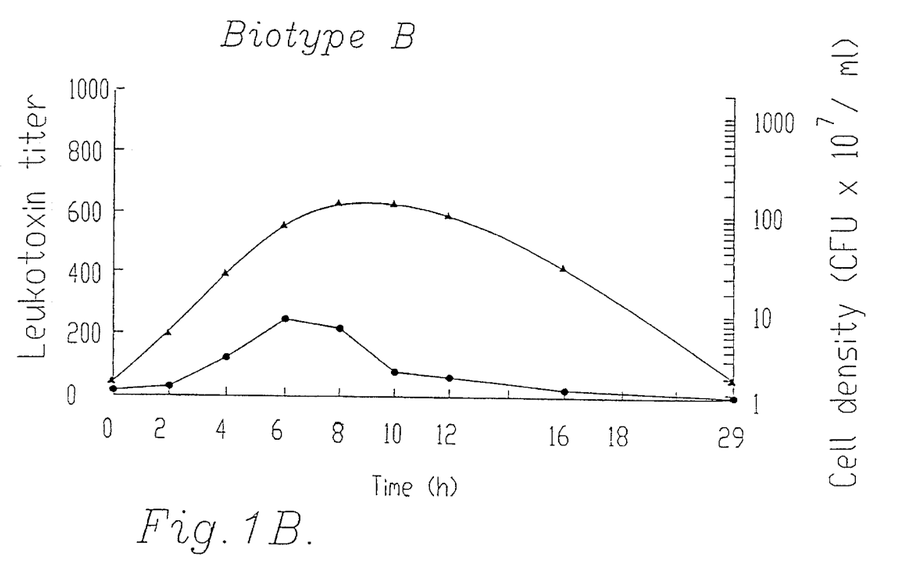
FIG. 1B is a graph illustrating leukotoxin production (dot data points) in relation to growth of a representative strain of biotype B of *F. necrophorum* (triangular data points), grown in anaerobic BHI broth.

The production of toxin by both biotypes increased with increasing bacterial growth, peaked at latelog and early-stationary phases, and then declined precipitously (FIGS. 1A and 1B). The leukotoxicity almost completely disappeared after 16 hours incubation. Culture supernates from biotype A had higher leukotoxin titer at all growth phases, although both biotypes had a similar cell density. The average leukotoxin titers for 11 biotype A strains and 16 biotype B strains were 882 and 56, respectively. The ranges of leukotoxin titer for biotype A and biotype B were 160–1172 and 0–162, respectively. Four out of 16 biotype B strains did not produce detectable levels of leukotoxin.

Culture Medium, pH, and Incubation Temperature

Figure 2A:
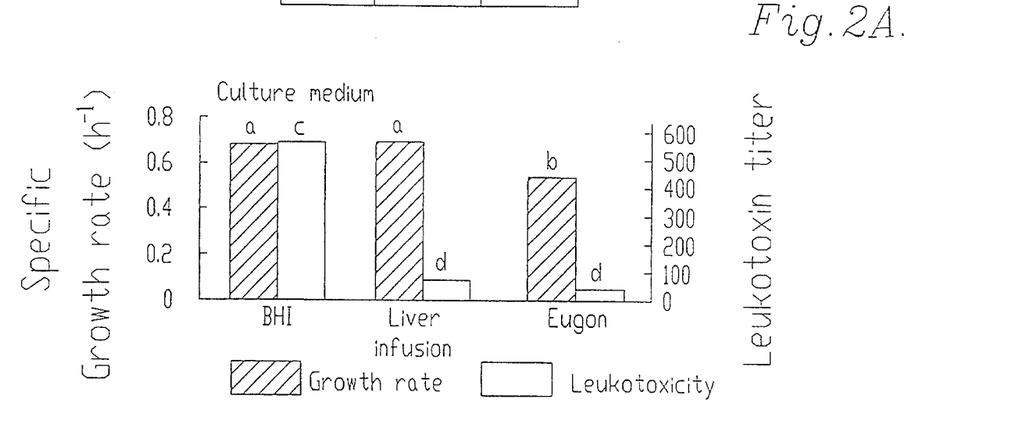
FIGS. 2A, 2B and 2C are respectively graphs showing the effects of culture medium, medium pH and incubation temperature on specific growth rate and leukotoxicity of *F. necrophorum*; samples for leukotoxin assay were obtained at late-log phase, and bars with different letters within each figure indicate significant difference at $p<0.05$ for culture medium and temperature, and at $p<0.10$ for pH.
Figure 2B:
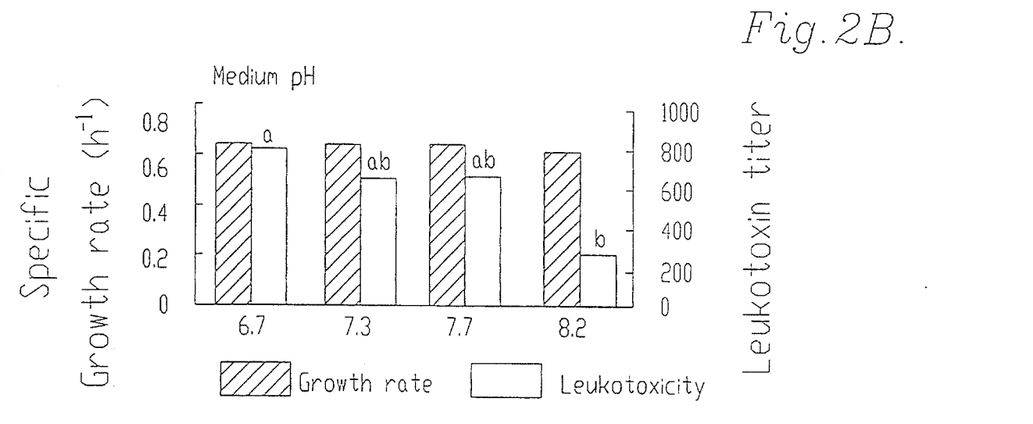
Figure 2C:
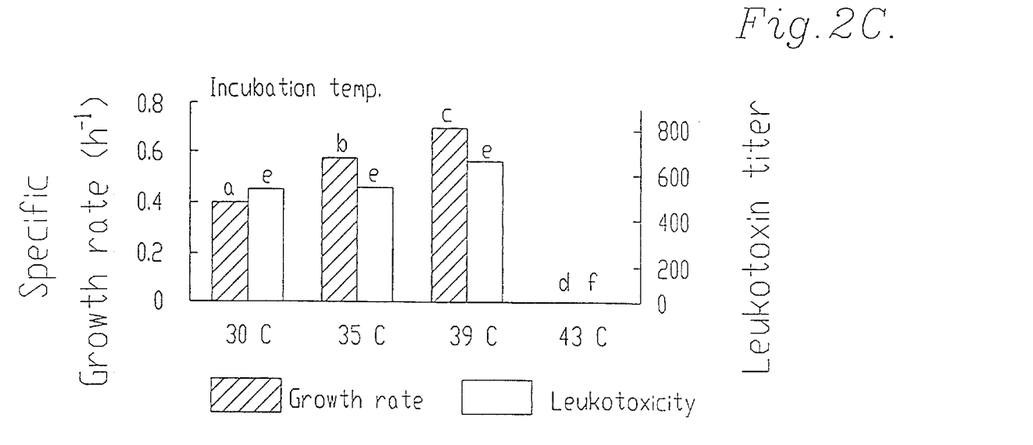

Among the cultural media tested, BHI and liver infusion broths supported highest bacterial growth (FIG. 2A). The specific growth rates were $0.69\ h^{-1}$ and $0.70\ h^{-1}$, with doubling times of 60 minutes and 59 minutes, in BHI and liver infusion broths, respectively. However, leukotoxin activity was higher ($p<0.05$) in culture grown in BHI than in Liver infusion broth. $F.\ necrophorum$ grew slowly (specific growth rate=$0.55\ h^{-1}$ and doubling time=76 minutes) in Eugon broth and produced minimal toxin. pH of medium from 6.7 to 8.2 had no ($<0.05$) effect on the growth rate, but leukotoxicity was lower ($p<0.1$) in the culture with pH 8.2 than in that with pH 6.7 (FIG. 2). The maximum leukotoxin activity was obtained in the culture incubated 39° C., which was the optimum temperature for growth (FIG. 2). No growth was observed at 43° C.

Redox Potential

Both growth rate and leukotoxin titer were low in oxidized BHI broth (Table 1). However, the addition of potassium ferricyanide to increase medium Eh from +170 to +375 mV had no ($p<0.05$) additional effect on the growth rate and leukotoxicity. Bacterial growth rate in anaerobic medium without any reducing agent was low ($0.40\ H^{-1}$). The addition of reducing agents, increased ($p<0.05$) the growth rate except, TC at low (0.32 mm) and DTT at high (3.8 mm) concentrations. The optimal Eh for $F.\ necrophorum$ growth appeared to be in the range of −230 to −280 mV, which required 1.4 µM of cysteine HCl, 3.2 µM of DTT, or 1.0 µM TC in the medium. These are within the range of concentrations normally used for anaerobic media (Costilow, 1981). The addition of cysteine HCl to the medium gave maximal leukotoxin titer (974–1,413), which was reflective of the high growth rate ($0.50$–$0.60\ h^1$). However, leukotoxicity in the cultures containing TC and DTT did not correspond to the growth rate. DTT (at 7.78 mM) and TC supported bacterial growth but caused low leukotoxin titer. In TC-reduced medium, leukotoxin titer decreased as the concentration of TC increased.

Iron Concentration

Figure 3:
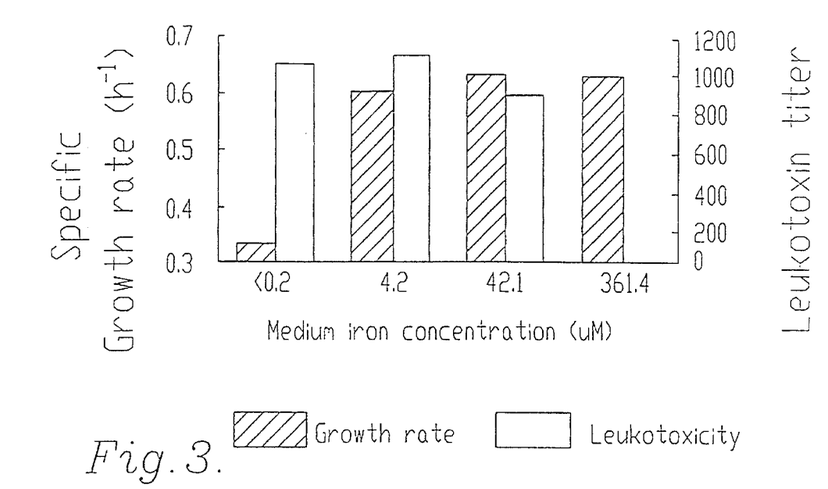
FIG. 3 is a graph depicting the effect of iron concentration on specific growth rate and leukotoxicity of *F. necrophorum* grown in anaerobic BHI broth with different iron concentrations; samples for leukotoxin assay were obtained at late-log phase, and bars with different letters indicate a significant difference at $p<0.05$.
Figure 4:
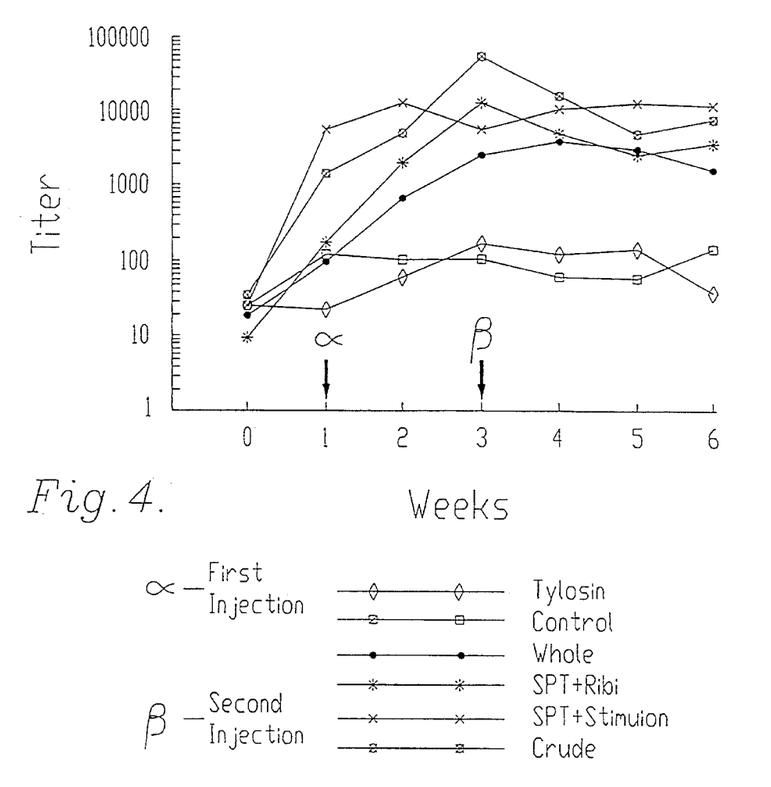
FIG. 4 is a graph that presents the serum leukotoxin neutralizing antibody titer determined over a six week testing interval that is described in Example 3.

Iron-exchange resin treatment of BHI broth decreased medium iron concentration from 6.1 µM to <0.2µM. In preliminary studies, resin-treated medium did not support $F.\ necrophorum$ growth unless $Ca^{2+}$ and $Mg^{2+}$ were added to it. $F.\ necrophorum$ exhibited slower ($p<0.05$) growth rate in the iron-limited medium than in media supplemented with iron (FIG. 3). However, growth rate was not influenced by iron concentration in the supplemented media. Leukotoxin titers were similar in media containing iron at or below 42.1 µM. Although medium with 361.4 µM of iron supported bacterial growth, no leukotoxicity was detected in the culture supernatant.

TABLE 1

| Effect of Culture Medium Eh on Growth and Leukotoxicity of $F.\ necrophorum$ | | | | |
|---|---|---|---|---|
| Medium and Oxidizing or Reducing Agent Added | Concentration (mM) | Eh (mV) | Specific Growth Rate ($h^{-1}$) | Leukotoxin Titer |
| Aerobic Medium[a] | | | | |
| None | 0 | +170 | .33 | 86 |
| Potassium ferricyanide | .77 | +375 | .28 | 60 |
| Anaerobic medium[b] | | | | |
| None | 0. | −103 | .40 | 971 |
| Cysteine HCl | .14 | −179 | .50[c] | 974 |
|  | .57 | −238 | .54[c] | 1286[c] |
|  | 1.42[d] | −242 | .63[c] | 1348[c] |
|  | 3.41 | −249 | .60[c] | 1413[c] |
| Dithiothreitol | .32 | −155 | .48[c] | 896 |
|  | 1.30 | −230 | .57[c] | 1040 |
|  | 3.24[d] | −276 | .57[c] | 1063 |
|  | 7.78 | −325 | .53[c] | 327[c] |
| Titanium (III) citrate | .25 | −106 | .45 | 226[c] |
|  | .50[d] | −147 | .50[c] | 76[c] |
|  | .99[d] | −217 | .51[c] | 76[c] |
|  | 1.96[d] | −262 | .59[c] | 40[c] |
|  | 2.91 | −310 | .52[c] | 10[c] |

TABLE 1-continued

Effect of Culture Medium Eh on Growth
and Leukotoxicity of *F. necrophorum*

| Medium and Oxidizing or Reducing Agent Added | Concentration (mM) | Eh (mV) | Specific Growth Rate ($h^{-1}$) | Leukotoxin Titer |
|---|---|---|---|---|
| | 3.85 | −352 | .43 | 4[c] |

[a]BHI broth was not boiled to remove dissolved oxygen.
[b]BHI broth was boiled until resazurin turned from purple to colorless.
[c]Growth rate or leukotoxicity in anaerobic medium with reducing agent was different ($p < 0.05$) from that without agent added.
[d]Concentration normally used to prepare anaerobic medium.

DISCUSSION

Previous studies on leukotoxin of *F. necrophorum* have used culture after 18 hours (Roberts, 1970; Coyle-Dennis and Lauerman, 1978; Emery et al., 1984; Emery et al., 1986), 3–4 days (Scanlan et al., 1982), or 7 days (Fales et al., 1977) of incubation. Emery et al. (1984) have indicated that leukotoxin production was critically affected by cell concentration and period of incubation. Leukotoxin titer was above 1,000 in 18-hour culture, with an approximate bacterial concentration of $10^9$ cells/ml, but 3-d culture supernate had much lower leukotoxicity. In the present example, maximal toxin production occurred at late-log and early stationary phases and was followed by a precipitous decline in leukotoxicity in both A and B biotypes. As indicated, the rapid decrease in leukotoxicity after stationary-phase may have been due to degradation of toxin possibly by proteolytic enzyme(s) produced by the bacteria. *F. necrophorum* produces proteolytic enzymes (Wallace and Brammall, 1985). Because leukotoxin is a protein (Garcia et al., 1975a; Coyle-Dennis and Lauerman, 1978) inactivation by proteolytic enzymes appears to be the logical reason for precipitous decline in leukotoxicity.

Scanlan et al. (1986) reported that *F. necrophorum* biotype A produced more leukotoxin that biotypes AB and B. The percentages of macrophage death by culture filtrate from biotypes A, AB and B were 93%, 77% and 21%, respectively. In the present study with 27 strains, the average of leukotoxin titer was approximately 18 times higher for biotype A than that for biotype B. The difference in toxin production by biotypes may account for the fact that biotype A is more virulent and more frequently encountered in hepatic abscesses than biotype B (Scanlan and Hathcock, 1983). Although samples for toxin assay were obtained at the same growth stage (late-log phase), a considerable strain-to-strain variation in toxin production was observed. Toxin titers were in excess of 1,000 in some strains whereas no toxicity was detected in others. The nonleukotoxin-producing strains were hemolytic and formed sediment in the liquid medium, and thus did not meet the criteria for nonpathogenic biotype C (Fievez, 1963).

Emery et al. (1984) reported that leukotoxin production was higher in Eugon or modified Eugon broth than in nutrient or thioglycollate broth. However, in the present example, Eugon broth was the least supportive of the three media tested for growth and leukotoxin production while BHI was the most supportive. The reason for the influence of medium on toxin production was unclear. Various culture media have been used to study leukotoxin production by *F. necrophorum*. These included M-1 continuous dialysis sac culture (Fales et al., 1977; Scanlan et al., 1982), Eagles minimal essential medium (Fales et al., 1977), modified thioglycollate broth (Coyle-Dennis and Lauerman, 1979), BHI agar (Scanlan et al., 1982) and modified heart infusion broth (Kanoe et al., 1985). medium with pH 8.2 supported *F. necrophorum* growth but not leukotoxin production. The stability of leukotoxin to extreme pH (4.0–9.0) has been reported (Emery et al., 1984; Scanlan et al., 1986). Therefore, high pH may affect production rather than activity of the leukotoxin.

Because liver is a highly vascularized organ, with blood EH around +126 to +422 (Meynell, 1963), it is of interest to know the influence of culture medium Eh on growth and leukotoxin production by *F. necrophorum*. A number of investigators (Hentges and Maier, 1972) have suggested that the growth of anaerobic bacteria is primarily effected by Eh of the medium. In contrast, it is postulated that the efficacy of reducing agents in promoting the growth of anaerobic organisms is due entirely to their oxygen-removing properties (O'Brien and Morris, 1971); both may be important (Hentges and Maier,1972). In this example, oxygen was excluded by boiling and with the use of oxygen-free $CO_2$ prior to adding reducing agent. Therefore, the higher growth rate in low-Eh medium, indicated that Eh did effect growth. In order to grow and set up infection in liver. *F. necrophorum* has to overcome the aerobic environment. Aerobic or facultative bacteria, such as *Actinomyces pyogenes* and *Streptococcus spp*, have been isolated frequently with *F. necrophorum* in liver abscesses (Kanoe et al., 1976; Berg and Scanlan, 1982; Lechtenberg et al., 1988). It is postulated that a synergistic interaction exists between *F. necrophorum* and facultative bacteria in the liver. The facultative organisms may utilize oxygen and lower Eh in host tissue to enable *F. necrophorum* growth (Beveridge, 1934; Roberts, 1970; Takeuchi et al., 1983; Brook and Walker, 1984). However, *F. necrophorum* is often isolated in pure culture in liver abscesses. Also, liver abscesses in mice and cattle have been experimentally induced by the injection of *F. necrophorum* alone (Takeuchi et al., 1984; Itabisashi et al., 1987); Lechtenberg and Nagaraja, 1991). It is known that *F. necrophorum* has a potent endotoxic lipopolysaccharide (Hofstad and Kristoffersen, 1971; Garcia et al., 1975b; Warner et al., 1975; Berg and Scanlan, 1982). This endotoxin and other components such as hemagglutinin of *F. necrophorum* cause platelet aggregation and may induce focal intravascular coagulation (Forrester et al., 1985; Kanoe and Yamanka, 1989). This may result in an anaerobic microenvironment in which *F. necrophorum* will grow. Platelet aggregation is induced only by biotype A (Forrester et al., 1985), which explains why biotype A is frequently isolated in pure culture (Berg and Scanlan, 1982); Lechtenberg et al., 1988).

A high concentration of TC (3.0 mM) had a detrimental effect on the growth of *F. necrophorum*. The inhibitory effect of TC on ruminal bacteria has been reported (Wachenheim and Hespell, 1984). The decrease in leukotoxicity was related to the strength and concentration of the reducing agent. TC was the strongest reducing agent among the three and inactivated the toxin greatly even at a low concentration (0.25 mM). Presumably, reducing agents structurally alter the toxin, a protein substance, by reducing disulfide bonds.

As with many other pathogenic bacteria (Bjorn et al., 1979; Filed et al., 1986; Kadurugamuwa et al., 1987) F. necrophorum requires iron as a growth factor. The availability of iron to microorganism is limited because of the competition from host iron-binding proteins such as transferrin and lactoferrin (Finkelstein et al., 1983). To acquire the iron essential for their growth and metabolism, the microbes have to complete with the host for iron. The hemolytic activity of F. necrophorum has been reported (Garcia et al., 1975a; Abe et al., 1979; Kanoe et al., 1984; Emery et al., 1985); Hemolysins break down erythrocytes and cause iron release. Therefore, the hemolytic activity of F. necrophorum may possibly aid in acquiring iron from the host. Also, it has been demonstrated that some pathogenic bacteria produce iron chelators (siderophores) to acquired iron (Finkelstein et al., 1983; Field et al., 1986). Whether or not F. necrophorum produces iron chelators is not known.

The association of availability of iron with toxin production has been reported in a number of studies. Gentry et al. (1986) indicated that the rate of leukotoxin production in Pasteurella haemolytica was enhanced by iron-containing and iron-chelating compounds. Strathdee and Lo (1989) later found that the leukotoxin determinant was composed of four contiguous genes and the expression of the toxin was greatly reduced by iron limitation. In contrast, the production of diphtheria toxin in Corynebacterium diphtheria (Murphy et al., 1978) and of exotoxin A in Pseudomonas aeruginosa (Bjorn et al., 1979; Woods et al., 1982) was inhibited by the presence of iron. In the present example, leukotoxicity of F. necrophorum was not affected by iron except at a high concentration (361.4 µM). Leukotoxicity was reduced but the growth of F. necrophorum was unaffected in medium containing high iron concentration. Therefore, the activity rather than production of the toxin appeared to be affected by high concentration of iron. These results demonstrate that growth conditions influence leukotoxin production by F. necrophorum. However, it should be emphasized the conditions like pH and Eh were not regulated or monitored through the incubation. Therefore, it is likely that the initial measurements may not be reflective of the conditions existing throughout the growth period.

EXAMPLE 2

The following example sets forth exemplary methods for the inactivation of leukotoxin supernate and inactivation of an entire culture, in order to produce vaccines for use in immunizing ruminant animals, such as cattle and sheep.

Inactivation of whole culture or culture supernate containing leukotoxin is preferably carried out by adding formalin (0.3–0.4%) or β-propiolactone (0.10–0.12%) on a vol/vol basis. Inactivated whole cultures are chilled in an ice bath and refrigerated for two days. If β-propiolactone is used, any residuum thereof is hydrolyzed by heating the cultures at 39° C. for 4–6 hours. Inactivation of whole cultures is tested by streaking the samples on BHI blood agar (reduced with 0.05% cysteine hydrochloride) and incubating the plates anaerobically for 24 hours. The resultant plates should exhibit no growth. The completed vaccine can be administered in a variety of ways, such as by intramuscular or parenteral injections.

EXAMPLE 3

The following example provides exemplary methods for the production of vaccine, and the prophylactic use thereof against F. necrophorum.

Thirty Holstein steers weighing 200–370 kg each were immunized with leukotoxin from F. necrophorum in a sixty-three day immuno-challenge test to determine whether serum leukotoxin neutralizing antibodies would protect against F. necrophorum. Prior to the initial immunization on day zero, ultrasonographic scanning confirmed that all animals were free from liver abscesses. Blood sample measurements were conducted according to the standard MTT-dye reduction neutralization assay for determination of the baseline serum leukotoxin neutralizing antibody titer. The thirty steers were randomly divided into six groups of five, and each group was injected with different inoculum preparations, as described below, through the administration of one subcutaneous injection on each of days 0 and 21.

Several anaerobic broth culture tubes were prepared to hold cultures of F. necrophorum for subsequent use. The broth culture preparation process began with an existing F. necrophorum, strain 25A (biotype A), culture, which was inoculated onto an anaerobic BHI blood agar, and incubated at 39° C. in an anaerobic Glove Box (Forma Scientific Co.) for 24 hours to obtain isolated colonies. Anaerobic BHI blood agar was prepared by prereducing commercial BHI broth with 0.05% by volume cysteine hydrochloride, and then dispensing 15 ml of the broth under nitrogen into each of several tubes containing respective 300mg portions of agar. Additionally, a 0.001% by volume portion of resazurin was included in the medium as a redox potential indicator. The tubes were closed with butyl rubber stoppers, crimped with aluminum seals, and autoclaved for 15 minutes. Any tubes showing pink coloration (a sign of oxidation) were discarded. The autoclaved tubes were placed inside the Glove Box, and cattle blood was pipetted into the tube to reach a 5% by volume blood portion (0.75 ml). The tubes were stoppered and gently mixed by inverting the tube, and the culture therein was poured into sterile petri plates. Blood agar plates were kept in the Glove Box, and used for culturing after at least 24 hours had passed for equilibration. Single colonies of F. necrophorum from the blood agar plates were inoculated with a loop into tubes containing 10 ml of anaerobic BHI broth. This anaerobic BHI broth was prepared as before, without agar, with prereduction, and anaerobic sterilization. The inoculated broth cultures inside the respective tubes were incubated at 39° C. for 6 to 9 hours. During culturing, the initial pH of 7.5 dropped to about 6.8. The preparation, dispensing, inoculation, and sample removal techniques employed were as described in Holdeman et al, Anaerobic Laboratory Manual, 4th Edition, Virginia Polytechnical Institute. The broth cultures were later used as inoculum for the introduction of F. necrophorum into larger cultures having a different medium from which leukotoxin test compositions were obtained for subsequent injection into the test animals. The test compositions included "inactivated cell culture," "crude toxin," and "semi-purified toxin."

"Inactivated cell culture" was prepared by treating active cell culture with formalin. Anaerobic BHI medium (VPI Anaerobic Culture System) was prepared according to standard methods in a 4 liter flask containing 3 liters of medium.

The flask was inoculated with 35 ml of log-phase *F. necrophorum*, strain 25A, culture, and incubated on a rocking platform at 39° C. for 6 to 8 hours ($A_{660}$=0.6 to 0.75). The cell culture, which had a count of $2.4 \times 10^8$ CFU/ml, was inactivated through the addition of formalin to achieve a 0.3% (v/v) formalin concentration.

"Crude toxin" was produced from filter-sterilized culture supernatant. Cell culture was prepared in the same manner as for inactivated cell culture. Supernatant was decanted after centrifugation of active culture at 13,500 g for 15 minutes (at 4° C. to protect the leukotoxin), and 1 ml was retained for a test of the leukotoxin activity.. The decanted supernatant was inactivated through the addition of formalin until the formalin concentration reached 0.3% (v/v). The inactivated supernatant was sterilized by filtration through a 0.45 μm membrane at 4° C.

"Semi-purified toxin" was prepared as a gel filtrate of concentrated crude toxin. Crude toxin was prepared as before, except in a 6 liter culture volume (two flasks). The crude toxin was subsequently subjected to concentration and filtration procedures to obtain semi-purified toxin as described in the paragraphs below.

In the concentration step, a 10K hollow fibre filter was installed in a hollow fibre concentration/desalting unit (Amicon DC10) according to the manufacturer's instructions. The filters were washed and conditioned in a series of steps: washing with 4 liters of distilled water; circulating 2 liters of double distilled water for at least one hour; and circulating 2 liters of PBS (pH 7.4) for at least 2 hours. After conditioning of the filters, the unit concentrated the 6 liters of culture supernatant filtrate to 100 ml at 4° C. The concentrated leukotoxin was dispensed in 3 ml aliquots and stored at −70° C. Two aliquots were retained for determination of leukotoxin titer and protein concentration.

The gel filtration step employed Sephacryl S300 gel from Pharmacia, which is suitable for molecular separation sizes ranging from $1 \times 10^4$ to $1.5 \times 10^6$. The filtration step used an elution buffer mixed with filter-sterilized double distilled water, phosphate buffer saline solution ("PBS") at pH 7.4, 10 μM $CaCl_2$, and 10 μM $MgCl_2$. The entire filtration procedure was performed at 4° C., in order to maintain the leukotoxin activity. The gel was packed in an XK 26/70 column according to the manufacturer's instructions. The lower end of the column was connected to a UV monitor and fraction collector. The column was pre-equilibrated with 350 ml of buffer, and 0.002% (w/v) blue dextran was added for determination of the column void volume. The concentrated leukotoxin was mixed with a 50% glycerol solution (aq.) in a 9:1 ratio (v/v) immediately prior to filtration. The 9 part volume of concentrated leukotoxin was selected to contain approximately 200 mg protein. The column was loaded with the mixture, which was filtered at a rate of 30 ml per hour.

Five ml fractions were collected after the protein began to elute from the column.

Group 1 was injected, in each instance, with 20 ml of vaccine formed from inactivated cell culture that was mixed with Ribi adjuvant-an oil emulsion adjuvant prepared by Ribi Immunochem of Hamilton, Montana. The Ribi adjuvant included 10% Drakeol 6VR light mineral oil (from Penreco of Butler, Pa.), 12% (w/v) lecithin (Centrolex P from Central Soya of Fort Wayne, Ind.), and 2.0 mg/ml synthetic trehalose dicorynemycolate (S-TDCM from Ribi Immunochem). The inactivated culture was diluted with sterile saline containing 0.4% (v/v) Tween 80 to a concentration equating to $2.4 \times 10^8$ CFU/ml, mixed with 10% (v/v) of Ribi adjuvant, and emulsified at 4° C.

Each steer in Group 2 was injected with 20 ml of crude toxin mixed with Ribi adjuvant. The crude toxin included 0.6 mg protein/ml or 15,640 leukotoxin units per ml before formalin treatment, which was mixed with 10% (v/v) of Ribi adjuvant per injection.

Each steer in Group 3 was injected with 4.6 ml of semipurified toxin mixed with Ribi adjuvant. The toxin preparation contained 10 mg protein (or 1,022,994 leukotoxin units) before formalin treatment, which was mixed with 10% (v/v) of Ribi adjuvant per injection.

The steers of Group 4 were each injected with 4.6 ml of semi-purified toxin mixed with Stimulon-21 adjuvant (QS-21 from Cambridge Biotech Corporation of Worcester, Massachusetts). The toxin preparation contained 10 mg protein (or 1,022,994 leukotoxin units) before formalin treatment, and the same was mixed with 100 μg of Stimulon-21 adjuvant per injection.

The steers of Group 5 were used as tylosin antibiotic (Tylan from Elanco Animal Health, Greenfield, Ind.) control animals. These were each injected with 10 ml of a solution containing PBS mixed with 10% (v/v) Ribi adjuvant. Subsequently, the steers were fed 100 mg of tylosin antibiotic per day mixed with 0.5 kg of ground corn.

The Group 6 steers were PBS controls that were created by mixing PBS with 10% (v/v) Ribi adjuvant and injecting 10 ml of this solution into the control animals.

Adjuvants, such as Ribi and Stimulon, work to promote antibody production in a nonspecific manner and, consequently, to enhance the general level of induced antibody production. As a measurement of this response, serum leukotoxin neutralizing antibody titers were monitored in the test animals throughout the study. After inoculation with leukotoxin on day zero, blood samples were collected every seven days until 42 days had passed, and the samples were tested to monitor the serum leukotoxin neutralizing antibody titer. Table 2 sets forth the results, which demonstrate that a maximum titer of 59,278 occurred for the crude supernatant plus Ribi group during week three.

TABLE 2

SERUM LEUKOTOXIN NEUTRALIZING ANTIBODY TITER

| | | Test Grouping* | | | | |
|---|---|---|---|---|---|---|
| Week | (1) Whole Cell Culture | (2) Crude Supernatant plus Ribi | (3) Semi-Purified Toxin plus Ribi | (4) Semi-Purified Toxin plus Stimulon | (5) Tylosin | (6) Control |
| 0 | 19 | 36 | 10 | 26 | 26 | 26 |
| 1 | 97 | 1,572 | 185 | 6,063 | 24 | 125 |
| 2 | 765 | 5,378 | 2,122 | 13,767 | 64 | 110 |
| 3 | 2,893 | 59,278 | 13,905 | 6,374 | 187 | 116 |

TABLE 2-continued

SERUM LEUKOTOXIN NEUTRALIZING ANTIBODY TITER

| | Test Grouping* | | | | | |
|---|---|---|---|---|---|---|
| Week | (1) Whole Cell Culture | (2) Crude Supernatant plus Ribi | (3) Semi-Purified Toxin plus Ribi | (4) Semi-Purified Toxin plus Stimulon | (5) Tylosin | (6) Control |
| 4 | 4.675 | 17,327 | 5,271 | 11,849 | 138 | 67 |
| 5 | 3,533 | 5,541 | 3,134 | 14,320 | 171 | 72 |
| 6 | 2,100 | 9,136 | 4,447 | 14,618 | 48 | 176 |

*Vaccines were given on days 0 and 21.

On day 42, through the use of an ultrasound-guided percutaneous catheterization procedure, the immune response of each steer was challenged by injecting inoculum taken from an active, seven hour culture of F. necrophorum, strain 25A. Various comparative methods were thereafter employed to monitor the impact of F. necrophorum infection upon the challenged animals. The liver of each steer was ultrasonographically scanned on days 42, 49, and 63. After the last scan, the steers were euthanized and necropsied to examine the respective livers for abscesses. The results are presented in Table 3 below. The Group 2 results indicate that crude toxin mixed with Ribi constituted the most effective prophylactic with regard to the prevention of liver abscesses, i.e., no incidence of liver abscesses as confirmed by necropsy versus 100% in the PBS control.

TABLE 3

INDUCED LIVER ABSCESS RESULTS COMPARISON

| Group | Number of Animals | Mortality | Liver Abscesses | | |
|---|---|---|---|---|---|
| | | | Ultrasonography | Necropsy | Incidence |
| (1) Whole Cell Culture Plus Ribi | 5 | 1* | 2/4 | 3/5 | 60 |
| (2) Culture supernatant plus Ribi | 5 | 0 | 0/5 | 0/5 | 0 |
| (3) Semipurified toxin plus Ribi | 5 | 0 | 1/5 | 2/5 | 40 |
| (4) Semipurified toxin plus Stimulon | 5 | 0 | 1/5 | 2/5 | 40 |
| (5) Tylosin | 5 | 0 | 2/5 | 4/5 | 80 |
| (6) PBS Control | 5 | 1** | 3/4 | 5/5 | 100 |

*Died of respiratory infection -- liver had no abscesses.
**Died of respiratory infection -- liver had abscesses.

REFERENCES

Abe, P. M, Kendall, C. J., Stauffer, L. R. and Holland, J. W., 1979. Hemolytic activity of Fusobacterium necrophorum culture supernatants due to presence of phospholipase A and lysophospholipase. Am. J. Vet. res., 40:92–96.

Berg, J. n. and Scanlan, C. M., 1982. Studies of Fusobacterium necrophorum from bovine hepatic abscesses; biotypes, quantitation, virulence, and antibiotic susceptibility. Am. J. Vet. Res., 43:1580–1586.

Beveridge, W. I. B., 1934. A study of twelve strains of Bacillus necrophorus, with observations on the oxygen intolerance of the organism. J. Patholo and Bacteriol., 38:467–491.

Bjorn, M. J., Sokol, P. A. and Iglewski, B. H., 1979. Influence of iron on yield of extracellular products in Pseudomonas aeruginosa cultures. J. Bacteriol., 138:193–200.

Brook, I., Hunter, V. and Walter, R. I., 1984. Synergistic effect of Bacteroides, Clostridian, and Fusobacterium, anaerobic cocci, and aerobic bacteria on mortality and induction of subcutaneous abscesses in mice. J. Infect. Dis., 149:924–928.

Costilow, R. N., 1981. Biophysical factors in growth. In: R. Gerhardt, R. G. E. Murray, R. N. Costilow, E. W. Nester, W. A. Wood, N. R. Krieg, and G. B. Phillips (Editors), Manual of Methods for General Bacteriology. American Society for Microbiology, Washington, D.C., pp. 66–78.

Coyle-Dennis, J. E. and Lauerman, L. H., 1978. Biological and chemical characteristics of Fusobacterium necrophorum leukotoxin. AM. J. Vet. Res., 39:1790–1793.

Coyle-Dennis, J. E. and Lauerman, L. H., 1979. Correlations between leukocidin production and virulence of two isolates of Fusobacterium necrophorum. Am. J. Vet. Res., 40:274–287.

Emery, D. L., Duffy, J. H. and Clark, B. L., 1984. Biochemical and functional properties of a leukocidin produced by several strains of Fusobacterium necrophorum. Aust. Vet J., 61:382–386.

Emery, D. L., Edwards, R. D. and Rothel, J. S., 1986. Studies on the purification of the leucocidin of Fusobacterium necrophorum and its neutralization by specific antisera. Vet. Microbiol., 11:357–372.

Emery, D. L., Vaughan, J. A., Clark, B. L. , Dufty, J. H. and Stewart, D. J., 1985. Cultural characteristics and virulence of strains of F. necrophorum isolated from the feet of cattle and sheep. Aust. Vet. J., 62:43–46.

Fales, W. H., Warner, J. F. and Teresa, G. W., 1977. Effects of Fusobacterium necrophorum leukotoxin in rabbit peritoneal macrophages in vitro. Am. J. Vet. Res., 38:491–495.

Field, L. H., Headley, V. L., Payne, S. M. and Berry, L. J., 1986. Influence of iron on growth, morphology, outer membranae protein composition, and synthesis of siderophores in Campylobacter jejuni. Infect. Immun., 54:126–132.

Fievez, L., 1963. Etude comparee des Souches de Sphaerophorus necrophorus isolees chez l'Homme et chez l'Animal. Presses Academiques Europeennes, Bruxelles.

Finkelstein, R. A., Sciortino, C. V. and Mcintosh., M. A., 1983. Role of iron in microbe-host interactions. Rev. Infect. Dis., 5(suppl.4):S759–777.

Forrester, L. J., Campbell, B. J., Berg, J. N. and Barrett, J. T., 1985. Biological characterization of Fusobacterium necrophorum. J. Clin. Microbiol., 22:245–249.

Garcia, M. M., Alexander, D. C. and McKay, K. A., 1975. Biological characterization of Fusobacterium necrophorum cell fractions in preparation for toxin and immunization studies. Infect. Immun., 11:609–611.

Garcia, M. M., Charlton, K. M. and McKay, K. A., 1975. Characterization of endotoxin from *Fusobacterium necrophorum*. Infect. Immun., 11:371–379.

Gentry, M. J., Confer, A. W., Weinberg, E. D. and Homer, J. T., 1986. Cytotoxin (leukotoxin) production by Pasteurella haemolytica: requirement for an iron-containing compound. AM. J. Vet. Res., 47:1919–1923.

Hale, W. H., 1985. Liver abscesses and founder in feedlot cattle. Anim. Nutr. Health., Sep. 19–20.

Hentges, D. J., and Maier, B. R., 1972. Theoretical basis for anaerobic methodology. AM. J. Clin. Nutr., 25:1299–1305.

Hofstad, T. and Kristoffersen, T., 1971. Preparation and chemical characteristics of endotoxic lipopolysaccharide from three strains of Sphaerophorus necrophorus. Acta Pathol. Microbiol. Scand., Sect. B, 79:385–390.

Holdeman, L. V., Cato, E. P. and Moore, W. E. C. (Editors), 1977. Anaerobic Laboratory Manual. Virginia Polytechnic Institute. Anaerobic Laboratory, Blacksburg, Va., 152 pp.

Hungate, R. E., 1969. A roll tube method for cultivation of strict anaerobes. In:J. R. Norris and D. W. Ribbons (Editors), Methods in Microbiology. vol. 3B. Academic press. N.Y., pp. 117–132.

Itabisashi, T., Yamamoto, R. and Satoh, M., 1987. Ultrasonogram of hepatic abscesses in cattle inoculated with Fusobacterium necrophorum. Jpn. J. Vet. sci., 49:585–592.

Kadurugamuwa, J. L., Anwar, H., Brown, M. R. W., Shand, G. H. and Ward, K. H., 1987. Media for study growth kinetics and envelope properties of iron-deprived bacteria. J. Clin. Microbiol., 25:849–855.

Kanoe, M., Imagawa, H., Toda, M., Sato, A. and Inoue, M., 1976. Bacteriology of bovine hepatic abscesses. Jap. J. Vet. Sci., 38:263–268.

Kanoe, M., Ishii, T., Mixutani, K. and Blobel, H., 1986. Partial characterization of leukotoxin from *Fusobacterium necrophorum*. Zbl. Badf. Hyg. A., 261:170–176.

Kanoe, M., Kitamoto, N., Toda, M. and Uchida, K., 1984. Purification and partial characterization of *Fusobacterium necrophorum* haemolysin. FEMS Microbiol. Lett., 25:237–242.

Kanoe, M., and Yamanka, M., 1989. Bovine platelet aggregation by Fusobacterium necrophorum. J. Med. Microbiol., 29:13–17.

Koch, A. L., 1981. Growth measurement. In: P. Gerhardt, R. G. E. Murray, R. N. Costilow, E. W. Nester, W. A. Wood, N. R. Krieg, and G. B. Phillips (Editors), Manual of Methods for General Bacteriology. American Society for Microbiology, Washington, D.C., pp. 182–217.

Lechtenberg, K. F. and Nagaraja, T. G., 1991. Hepatic ultrasonography and blood changes in steers with experimentally induced liver abscesses. Am. J. Vet. Res., 52:803–809.

Lechtenberg, K. F., Nagaraja, T. G., Leipold, H. W. and Chengappa, M. M., 1988. Bacteriologic and histologic studies of hepatic abscesses in cattle. Am. J. Vet. Res., 49:58–62.

Meynell, g.G. 1963. Antibacterial mechanism of the mouse gut. II. The role of Eh and volatile fatty acids in the normal gut. Br. J. Exp. Pathol., 44:209–214.

Murphy, J. R., Michel, J. L. and Teng, M., 1978. Evidence that the regulation of diphtheria toxin production is directed at the level of transcription. J. Bacteriol., 135:511–516.

O'Brien, R. W. and Morris, J. G., 1971. Oxygen and the growth and metabolism of *Clostridia acetobutylicum*. J. Gen Microbiol., 68:307–318.

Reddy, P. G., McVey, D. S., Chengappa, M. M., Blecha, F., Minocha, H. C. and Baker, P. E., 1990. Bovine recombinant granulocyte-macrophage colony-stimulating factor enhances bovine neutrophil functions in vitro. J. Am. Vet. Med. Assoc., 51:1395–1399.

Roberts, D. S., 1967. The pathogenic synergy of *Fusiformis necrophorus* and *Corynbacterium pyogenes*. II. The response of *F. necrophorum* to a filterable product of *C. pyogenes*. Br. J. Exp. Pathol., 48:674–679.

Roberts, D. S., 1970. Toxic, allergenic and immunogenic factors of *Fusiformis necrophorus*. J. Comp. Pathol., 80:247–257.

SAS, 1987. SAS/STAT Guide for Personal Computers. SAS Ins., Inc., Cary, N.C., 378 pp.

Scanlan, C. M., Berg, J. N. and campbell, F. F., 1986. Biochemical characterization of the leukotoxins of three bovine strains of *Fusobacterium necrophorum*. AM. J. Vet. res., 47:1422–1425.

Scanlan, C. M., Berg, J. N. and Fales, W. H., 1982. Comparative in vitro leukotoxin production of three bovine strains of *Fusobacterium necrophorum*. Am. J. Vet. Res., 43:1329–1333.

Scanlan, C. M., and Hathcock, T. L., 1983. Bovine rumenitis-liver abscess complex: A bacteriological review. Cornel Vet., 73:288–297.

Segel, I. H., 1976. Oxidation-reduction reactions. In:Biochemical Calculations. John Wiley and Sons. N.Y., p. 175.

Strathdee, G. A. and Lo, R. Y. C., 1989. Regulation of expression of the *Pasteurella haemolytica* leukotoxin determinant. J. Bacteriol., 171:5955–5962.

Takeuchi, S., Nakajima, Y. and Hashioto, K., 1983. Pathogenic synergism of *Fusobacterium necrophorum* and other bacteria in formation of liver abscess in BALB/c mice. Jpn. J. Vet. Sci., 45:775–781.

Takeuchi, S., Nakajima, Y., Ueda, J., Motoi, Y., Kobayashi, Y. and Morozumi, T., 1984. Hepatic abscess formation in cattle inoculated with *Fusobacterium necrophorum*. Jpn. J. Vet. Sci., 46:339–344.

Vega, M. V., Maheswaran, S. K., Leininger, J. R. and Ames, T. R., 1987. Adaptation of a colorimetric microtitration assay for quantifying *Pasteurella haemolytica* A1 leukotoxin and antileukotoxin. AM. J. Vet. Res., 48:1559–1564.

Wachenheim, D. E. and Hespell, R. B., 1984. Inhibitory effects of titanium (III) citrate on enumeration of bacteria from rumen contents. Appl. Environ. Microbiol., 48:444–445.

Wallace, r. J. and Brammall, M. L., 1985. The role of difference species of bacteria in the hydrolysis of protein in the rumen. J. Gen. Microbiol., 131:821– 832.

Warner, J. F., Fales, W. H., Sutherland, R. C. and Teresa, G. W., 1975. Endotoxin from *Fusobacterium necrophorum* of bovine hepatic abscess origin. AM. J. Vet. Res., 36:1015–1019.

Woods, D. E., Sokol, P. A. and Iglewski, B. H., 1982. Modulatory effect of iron on the pathogenesis of

*Pseudomonas aeruginosa* mouse corneal infections. Infect. Immun., 35:461–464.

We claim:

1. The vaccine produced by the method comprising the steps of:

forming a culture of a biotype A strain of *F. necrophorum* bacteria in growth media;

causing said bacteria to grow in said culture, and to elaborate leukotoxin in a supernate, including the steps of culturing at a temperature of from about 35°–41° C. and a pH of from about 6.5–8 for a period of from about 4–10 hours, while preserving a substantial proportion of the elaborated leukotoxin; and forminq said vaccine by inactivating at least said leukotoxin supernate at the end of said culturing period.

2. An inoculum for immunizing ruminant animals against *F. necrophorum*, comprising:

an inactivated leukotoxin-bearing supernate taken from a culture of a biotype A strain of *F. necrophorum* cultured for a period of from about 4–9 hours; and a compatible carrier for said supernate.

3. The inoculum as set forth in claim 2, including an adjuvant.

* * * * *